United States Patent [19]

Summers

[11] Patent Number: 5,087,265
[45] Date of Patent: Feb. 11, 1992

[54] DISTAL ATHERECTOMY CATHETER

[75] Inventor: David P. Summers, Montgomery, Tex.

[73] Assignee: American BioMed, Inc., The Woodlands, Tex.

[21] Appl. No.: 383,606

[22] Filed: Jul. 24, 1989

Related U.S. Application Data

[63] Continuation-in-part of Ser. No. 312,737, Feb. 17, 1989, Pat. No. 4,994,067.

[51] Int. Cl.$^5$ ............................................. A61B 17/00
[52] U.S. Cl. ..................................... 606/159; 604/22
[58] Field of Search .................... 606/159, 167–171, 606/180; 604/22, 27, 53

[56] References Cited

U.S. PATENT DOCUMENTS

| | | | |
|---|---|---|---|
| 3,815,604 | 6/1974 | O'Malley et al. | |
| 3,844,272 | 10/1974 | Banko. | |
| 3,882,872 | 5/1975 | Douvas et al. | |
| 3,884,238 | 5/1975 | O'Malley et al. | |
| 4,011,869 | 3/1977 | Seiler, Jr. | |
| 4,111,207 | 9/1978 | Seiler, Jr. | |
| 4,167,943 | 9/1979 | Banko. | |
| 4,167,944 | 9/1979 | Banko. | |
| 4,203,444 | 5/1980 | Bonnell et al. | |
| 4,210,146 | 7/1980 | Banko. | |
| 4,323,071 | 4/1982 | Simpson et al. | |
| 4,411,055 | 10/1983 | Simpson et al. | |
| 4,513,745 | 4/1985 | Amoils. | |
| 4,577,629 | 3/1986 | Martinez. | |
| 4,589,412 | 5/1986 | Kensey. | |
| 4,589,414 | 5/1986 | Yoshida et al. | |
| 4,598,710 | 7/1986 | Kleinberg et al. | |
| 4,603,694 | 8/1986 | Wheeler. | |
| 4,616,648 | 10/1986 | Simpson et al. | |
| 4,616,652 | 10/1986 | Simpson et al. | |
| 4,631,052 | 12/1986 | Kensey. | |
| 4,651,753 | 3/1987 | Lifton. | |
| 4,661,094 | 4/1987 | Simpson et al. | |
| 4,662,869 | 5/1987 | Wright. | |
| 4,669,469 | 6/1987 | Gifford, III et al. | |
| 4,678,459 | 7/1987 | Onik et al. | |
| 4,681,106 | 7/1987 | Kensey et al. | |
| 4,685,458 | 8/1987 | Leckrone. | |
| 4,696,667 | 9/1987 | Masch. | |
| 4,728,319 | 3/1988 | Masch | 604/22 |
| 4,729,763 | 3/1988 | Henrie. | |
| 4,747,406 | 5/1988 | Nash. | |
| 4,747,821 | 5/1988 | Kensey et al. | |
| 4,749,376 | 6/1988 | Kensey et al. | |
| 4,765,332 | 8/1988 | Fischell et al. | |
| 4,771,774 | 9/1988 | Simpson et al. | |
| 4,772,258 | 9/1988 | Marangoni et al. | |
| 4,781,186 | 11/1988 | Simpson et al. | |
| 4,794,931 | 1/1989 | Yock. | |
| 4,819,635 | 4/1989 | Shapiro. | |
| 4,834,729 | 5/1989 | Sjostrom. | |
| 4,842,579 | 6/1989 | Shiber | 604/22 |
| 4,844,064 | 7/1989 | Thimsen et al. | |
| 4,850,354 | 7/1989 | McGurk-Burleson et al. | |
| 4,857,045 | 8/1989 | Rydell | 604/22 |
| 4,857,046 | 8/1989 | Stevens et al. | 604/22 |
| 4,883,458 | 11/1989 | Shiber | 604/22 |
| 4,895,560 | 1/1990 | Papantonakos | 604/22 |

*Primary Examiner*—Robert A. Hafer
*Assistant Examiner*—Kerry Owens
*Attorney, Agent, or Firm*—Gunn, Lee & Miller

[57] ABSTRACT

This disclosure sets out a catheter for bodily insertion. The catheter tip supports an elongate hollow housing with a window for occlusive material cutting, a cutter head on the interior rotates, driven by a drive wire in the hollow catheter tube. In addition, the cutter head reciprocates or oscillates to cut on its back edge, the edge trimming material entering through the window. The window and optional slots admit the unwanted material and enable trimming for a vacuum removal through the catheter tube. The window is urged into contact by a pair of flexed wires, the wires moving the housing into operative contact.

15 Claims, 3 Drawing Sheets

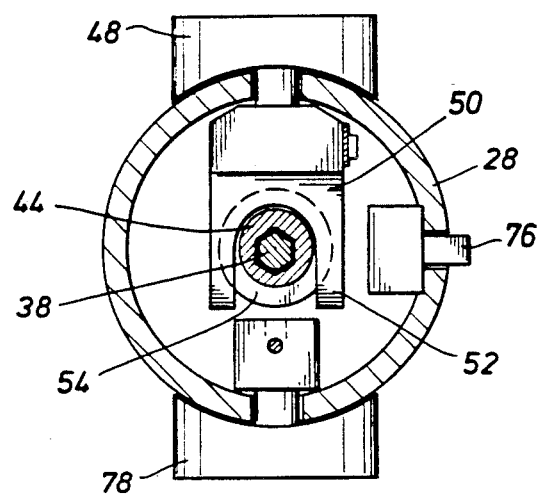
FIG.2
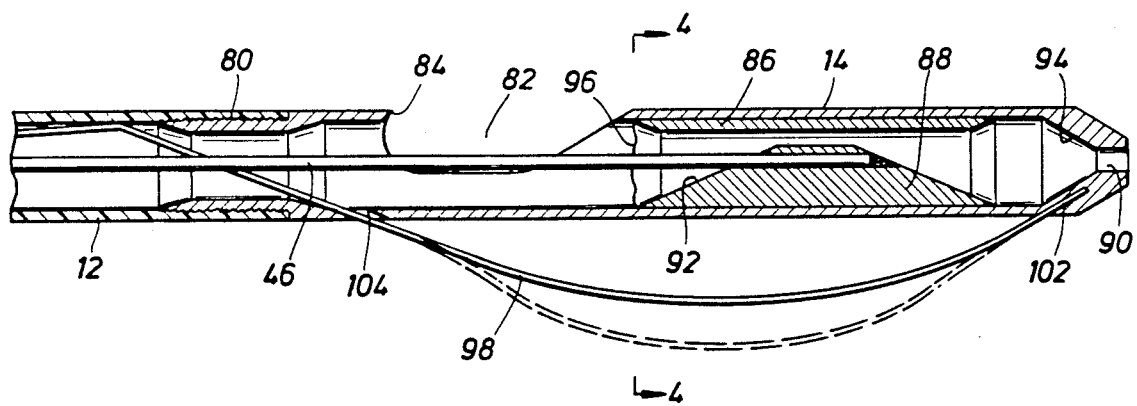
FIG.3
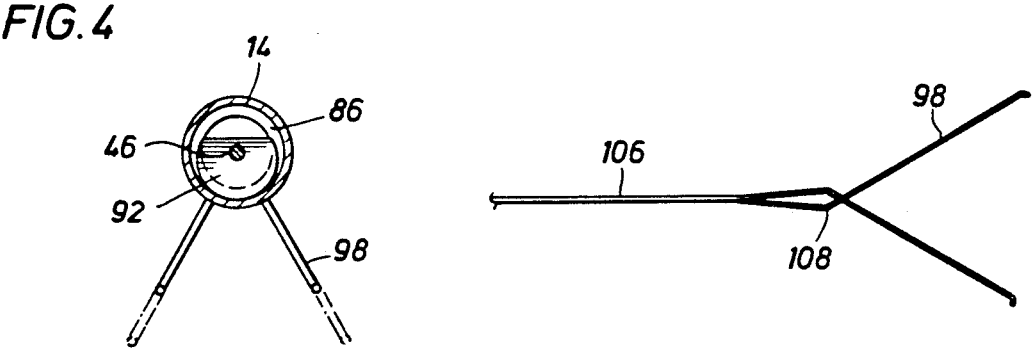
FIG.4
FIG.5

DISTAL ATHERECTOMY CATHETER

RELATED APPLICATIONS

This application is a continuation-in-part of patent application Ser. No. 07/312,737 filed Feb. 17, 1989 now U.S. Pat. No. 4,994,067.

BACKGROUND OF THE DISCLOSURE

The present invention is directed to an atherectomy catheter, particularly, a distal atherectomy catheter for use in the distal and coronary arteries where small vessel size and tortuosity present numerous problems of access.

Many technological advancements have been made in recent years for treatment of coronary disease. Surgical bypass techniques, such as coronary artery bypass graft surgery, are routinely performed and are highly successful. While the risks of bypass surgery have been minimized through technological advancements, opening of the chest cavity is still required. This requires special surgical skills and equipment which are not readily available in many areas. For many patients, a bypass operation may not be indicated and therefore various surgical techniques have been devised to treat occlusive coronary artery diseases of such patients. For example, various prior art devices have been developed for removing and/or compressing atherosclerotic plaque, thromboses, stenosis, occlusion, clots, embolic material, etc. from veins, arteries and the like.

One such device is disclosed in applicant's co-pending application Ser. No. 07/312,737 filed Feb. 17, 1989, which disclosure is incorporated by reference herein. In applicant's co-pending application, removal of occlusive material is accomplished by cooperative reciprocal action between an inner and outer catheter tube for excising occlusive material blocking the coronary vessel. While the apparatus of applicant's co-pending application has been successfully shown to remove occlusive material in laboratory tests, enhanced and more efficient removal of occlusive material may be achieved with the improved apparatus described herein. One feature which is important to the acceptability of a distal atherectomy catheter by the medical community is the efficiency and speed with which the lumen of an artery or the like may be unblocked to provide normal blood flow.

U.S. Pat. No. 4,650,466 (Luther) discloses an angioplasty device comprising a woven tube of metal or plastic fibers and a retraction stylet that are attached at one end of the catheter tube for insertion into a vein, artery, and the like for the removal of plaque and similar materials. One or more guide wires are attached to the woven tube for rotation and manipulation inside the artery. The woven tube is placed within the artery and expanded to contact the interior, plaque coated, wall of the artery. Movement of the expanded woven tube abrades the plaque from the arterial wall to form particles which are trapped within the woven tubes. The trapped plaque particles are removed with the angioplasty device upon its removal from the artery of the patient.

Other prior art devices include catheters fitted with an inflatable balloon for compressing occlusive materials such as plaque against the vessel wall. U.S. Pat. No. 4,273,128 (Lary) discloses a coronary cutting and dilating instrument for treatment of stenotic and occlusive coronary artery disease. The device disclosed therein includes a cutting and dilating instrument having one or more radially extending knife blades at a forward end thereof for making the coronary incision and an inflatable balloon for dilating the stenotic artery zone immediately after the incision.

Other angioplasty devices include a catheter having a motor driven cutting head mounted at its distal end. The cutting head is connected to the drive motor via a flexible drive shaft extending through the catheter. Extremely high rotational cutting head speeds have been achieved, in the range of 50,000-300,000 rpm, by these motor driven cutter heads. Various problems, however, have been associated with the use of the balloon tipped catheters and high speed cutting heads. The balloon catheter is expanded by injection of pressurized fluid into the balloon to expand it against the wall of the artery. Some problems which have been reported include the vessel dissection, perforation, rupture, conversion of a stenosis to an occlusion, and embolization. Furthermore, angioplasty devices utilizing balloons do not remove the plaque from the arterial wall but simply compress the plaque against the wall of the vessel. Thus, the stenosis or occlusion frequently reoccur requiring further treatment.

Atherectomy devices utilizing a motor driven high speed cutting head include a number of disadvantages. Heat dissipation and vibration is a problem. The path of the occlusion in an artery is often a tortuous path and therefore the lengthy flexible drive shaft connected to the cutter head must traverse a number of bends or curves. Consequently, as the flexible drive shaft rotates, it contacts the inner wall of the catheter resulting in localized heating and vibrations due to the frictional contact. This, of course, is very uncomfortable for the patient and may result in spasm, weakening or perforation of the vessel along the route of the catheter.

It is therefore one advantage of the present invention to provide an improved atherectomy catheter having a reciprocal rotary cutter head at the distal end thereof rotated at a relatively low speed in the range of 2,000 rpm to enhance patient comfort.

One notable feature of the invention to provide an atherectomy catheter for traversing the small and tortuous vasculature of the heart while having the ability to bore through a total obstruction and excise a hemispherical or circumferential section from the lumen of the vessel and entrap the excised section within a containment housing.

It is yet another object of the invention to provide an atherectomy catheter for progressively opening the lumen of a vessel, entrapping and discharging the excised obstructive material into a containment housing or discharge passage of the catheter until the entire obstruction has been removed leaving a smooth fissure and flap-free enlarged internal vessel diameter.

SUMMARY OF THE INVENTION

A distal atherectomy catheter is disclosed for removing obstructions, plaque, stenosis, occlusions, or the like from an artery or coronary vessel. The catheter comprises a flexible, hollow outer catheter tube housing a reciprocating, rotating or oscillating cutting element at its distal end. The cutting element is connected to a flexible drive shaft concentrically located within the outer tube. An annular return passage is defined by the outer catheter tube about the flexible drive shaft providing a discharge passage communicating with an external vacuum means for collection of occlusive cuttings removed by the cutting element from the artery or coronary vessel. A guide wire extends through the catheter tube and cutting element for guiding the catheter to the occluded site in a vessel. A deflection wire extends through the catheter and exits near its forward end. The exposed end of the deflection wire is welded, soldered or otherwise secured to the forward or leading end of the catheter for deflecting the catheter against the inner wall of the coronary vessel. The drive cable is connected to an external drive motor.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 2 is a sectional view of the invention taken along line 2—2 of FIG. 1;

FIG. 3 is a partial sectional view of the cutting head of the invention;

FIG. 4 is a sectional view of the cutting head of the invention taken along line 4—4 of FIG. 3;

FIG. 5 is a partial side view of the deflection wire of the invention;

DETAILED DESCRIPTION OF THE PREFERRED EMBODIMENT

Figure 1:
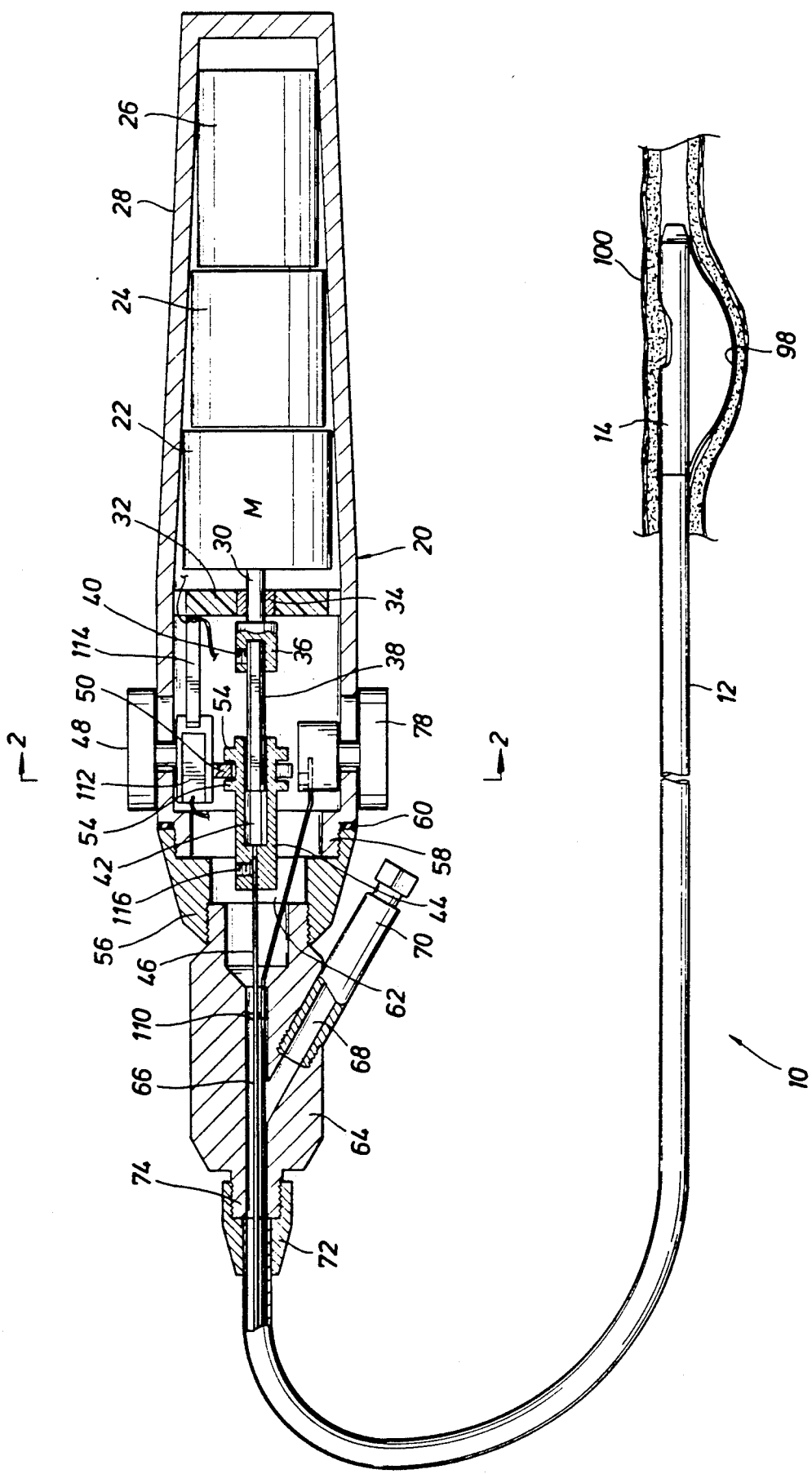
FIG. 1 is a partial sectional view of the atherectomy catheter of the invention.

Referring first to FIG. 1, the distal atherectomy catheter of the invention is generally identified by the reference numeral 10. The catheter 10 of the invention comprises a flexible outer catheter 12 which may be several feet in length. A cutter element housing 14 is threadably mounted or otherwise secured to the distal or forward end of the catheter tube 12. The proximal end of the catheter tube 12 is connected to a hand-held drive motor assembly generally identified by the reference numeral 20.

The motor assembly 20 includes a motor 22, battery or storage cell 24 and a charging coil 26 housed within a substantially cylindrical housing 28. The motor 22, battery 24 and charging coil 26 are securely retained within the housing 28 and are electrically connected to provide sufficient power to operate the catheter 10. A drive shaft 30 extends axially from the motor 22. The drive shaft 30 extends through and is supported by a brace 32 and a bushing 34 so that the drive shaft 30 rotates freely and shaft vibration is minimized. A coupling 36 is supported on the end of the drive shaft 30 for connection to a drive shaft extension 38. The drive shaft extension 38 is hexagonal or square in cross section and fixedly secured to the coupling 36 by set screw 40. The drive shaft extension 38 extends into and is received in an axial recess 42 of a drive wire coupling 44. The axial recess 42 is profiled to the shape of the drive shaft extension 38 for establishing a rotary connection between the flexible drive wire 46 and the drive shaft 30 connected to the rotary drive motor 22.

The drive wire coupling 44 is substantially cylindrical in shape and is centrally located within the handle housing 28. The axial recess 42 is of sufficient depth to permit the drive coupling 44 to be reciprocated along the length of the drive shaft extension 38 for reciprocally manipulating the cutting element of the apparatus 10 while maintaining rotary engagement of the drive wire 46 with the drive motor 22. The drive wire coupling 44 is manually reciprocated by moving the slide knob 48 to and fro. A drive fork 50 connects the slide knob 48 to the drive wire coupling 44. The drive fork 50, as best shown in FIG. 2, terminates in a pair of spaced arms 52 which extend about and engage the drive wire coupling 48 within a circumferential groove defined by a pair of spaced circumferential flange members 54 extending about the body of the drive wire coupling 44. The flange members 54 are sufficiently spaced and of adequate height to loosely engage the drive fork 50 so that rotation of the drive wire coupling 44 is not impeded even when the drive wire coupling 44 is manually reciprocated along the drive shaft extension 38.

The open end of the handle housing 28 is closed by a cap 56 which is threaded onto the exteriorly threaded end 58 of the housing 28. The point of connection is sealed by a gasket 60 which is slightly compressed when the cap 56 is fully threaded on the end 58 of the housing 28.

The cap 56 includes an axial passage 62 extending therethrough, a portion of which is interiorly threaded for connection with a Y fitting 64 threaded thereon. An axial passage 66 of reduced diameter but in alignment with the axial passage 62 extends through the Y fitting 64. A passage 68 angularly branching from the axial passage 66 provides an outlet connection for a cannula 70 providing access to the axial passage 36. The proximal end of the catheter tube 12 is attached to the Y fitting 64 by a catheter retainer cap 72 threadably connected to the externally threaded end 74 of the Y fitting 64.

Referring now to FIG. 2 an on/off switch 76 insures that the cutting element of the invention does not rotate while the catheter is being inserted into a patient. In the off position the drive motor 22 is opened so that the drive wire 46 is not rotated. A locater slide 78, to be described in greater detail hereinafter is located on the housing 28 opposite the slide knob 48.

Referring now to FIG. 3, the cutter head assembly of the invention is shown in greater detail. The cutter head assembly includes an outer tubular housing 14 threadably secured to the distal end of the catheter tube 12 at 80. A slot or port 82 is formed in the cutter housing 14 by removing a portion of the sidewall of the housing 14 providing access to the interior of the housing 14. The slot 82 defines a "duck bill" profile terminating at a point 84. The "duck bill" profile aides in grabbing the obstructive material to be excised. As the tissue or obstructive material enters the slot 82, it is pushed against the point 84 and speared and held stationary for removal by the cutter 86.

The cutter 86 is connected to the distal end of the flexible drive wire 46. The cutter 46 is substantially cylindrical in shape and partially hollow. A raised portion 88 interiorly located within the cutter 86 provides a connection point for the drive wire 46. The raised portion 88 does not totally obstruct the interior of the cutter 86 so that a passage is defined which permits a guide wire to be passed through the catheter 12, the cutter 86 and out a guide wire port 90 formed in the forward tip of the cutter housing 14. The sloped portion or ramp 92 of the raised portion 88 enables the guide wire (not shown in the drawings) to conveniently pass through the cutter 86. Likewise, the slope inner walls 94 of the forward tip of the housing 14 direct the guide wire so that it may be conveniently threaded through the port 90. The guide wire typically extends a short distance in advance of the housing 14 to aid in guiding the catheter of the invention in traversing the tortuous paths encountered in blood vessels, particularly the smaller blood vessels.

The proximal end of the cutter 86 forms a serrated cutting edge 96 for removing occlusive material, such as plaque which coats the arterial wall. To aid the efficiency of the cutter 86, bowed wires 98 are provided to force the cutter head against the interior arterial wall of an artery or blood vessel 100 as best shown in FIG. 1. The bowed wires 98 are connected to the forward tip of the cutter housing 14 at 102 and extend exterior of the cutter housing 14 through an opening 104. The wires 98 are welded or braised to a locater shaft 106 which extends the full length of the catheter 12 and is connected to the locator slide 78 which is manipulated back and forth to actuate the wires 98. Referring briefly to FIG. 5, it will be noted that the wires 98 are bent at 108 and crossed over each other. This permits the cutter head assembly to be correctly positioned against the wall of the artery 100. In operation, as the locater slide 78 is moved forward, the wires 98 extend into the artery 100 and spread outwardly slightly so that the cutter head assembly is centrally located between the spread wires 98 substantially as shown in FIG. 4. Rotation of the slide knob 78 in the clockwise direction will lock the locater wires 98 in the expanded position. If the catheter is to be rotated for further positioning, the wires 98 must be completely retracted flush with the cutter housing 14 so as to avoid any damage on contact of the wires 98 and the vessel wall. The wires 98 decentralize the structure of FIG. 3 in the vessel.

Referring again to FIG. 1, the operation of the catheter 10 will be described. The catheter 10 is typically inserted through the femoral artery of the patient and is directed by the physician to the site of the obstruction. If a guide wire is required, the guide wire is inserted through the cannula 70, through the catheter 12 and out the port 90 of the forward tip of the cutter housing 14. Once the cutter head assembly is properly positioned, the guide wire is removed and vacuum pump is connected to the cannula 70 for creating a vacuum within the catheter 12 for removal of severed or excised plaque or the like as it is severed by the cutter 86. A seal 110 in the passage 66 of the Y fitting 64 seals off the return passage so that plaque and the like is directed to a collection vessel connected to the cannula 70.

To operate the catheter 10 the switch 76 is positioned in the on position. However, when the cutter 86 is in the innermost position as shown in FIG. 3, it does not rotate because the electrical connection for providing power to the motor 28 is not yet complete. Referring to FIG. 1, the switch 48 is provided with a brass conductor strip 112 which must engage the brass conductor 114 to complete the circuit and provide electrical power to the drive shaft 30. As the slide 48 is slid backward toward the base of the handle 20, the contact between the conductor strip 112 and the brass conductor 114 is completed and the drive motor 22 is engaged resulting in rotation or oscillation of the drive wire 46 which is connected to the drive wire coupling 44 by a set screw 116. In this manner, the cutter 86 is rotated or oscillated in the range of 2,000 to 10,000 rpm while it is pulled toward the rear end of the cutter housing 14. As material is severed by the cutter 86, it is removed by the vacuum suction so that the severed material does not interfere with the cutting action of the cutter 86.

ALTERNATE EMBODIMENTS

Figure 6:
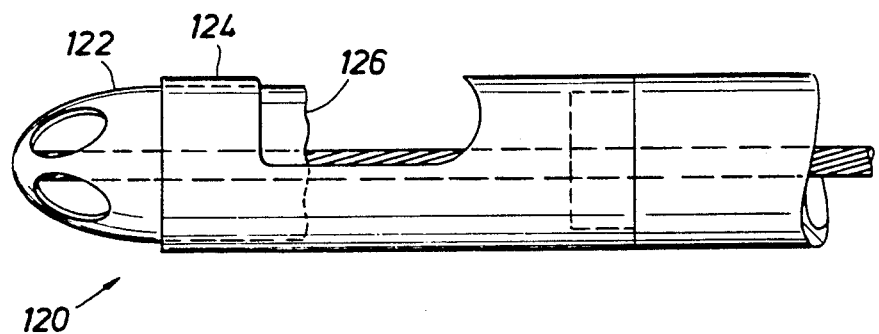
FIG. 6 is a partial side view of an alternate embodiment of the cutting head of the invention.

FIG. 6 is an embodiment 120 of the cutter head which includes a forward portion 122 which can extend out of, or in advance of, the cutter housing 124 and the cutter itself is hollow having a more or less conical forward portion which is slotted so that it can cut into any obstruction that is directly in advance. It can more or less bore through a total obstruction. The backside 126 of the blade still has the serrated cutting edge and it can operate in the same fashion as previously described regarding the first embodiment 10.

Figure 7:
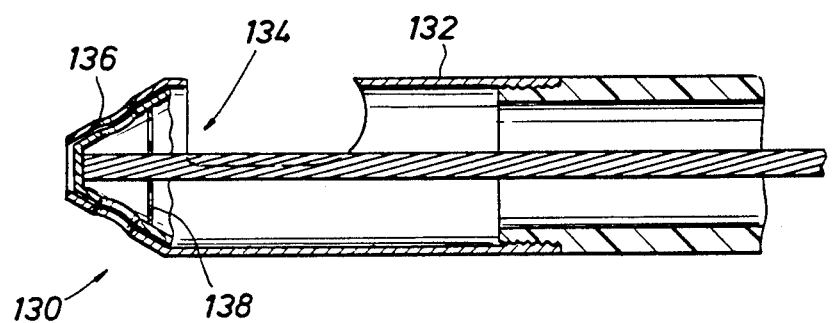
FIG. 7 is a partial side view of another alternate embodiment of the cutting head of the invention.

FIG. 7 is a similar structure 130 except that the conical cutter head is not exposed but it is enclosed within the forward conical portion of the cutter housing. The cutter housing 132 is slotted and the cutter head 134 is also slotted and is hollow and may also be provided with some cutting burrs to basically cut or scrape the material as it extends through the slots 136 in the outer conical surface. Again, it also has the serrated at the back edge blade so that it will continue to perform a cutting function as it is reciprocated backwardly and the drive shaft is optionally hollow to provide the return passage for any severed material captured within the hollow cutter head. A baffle 138 closes the cone portion of the cutter from the serrated end of the cutter. Hence, cuttings are entrapped in the cone and may be suctioned through the hollow drive wire if desired.

Figure 8:
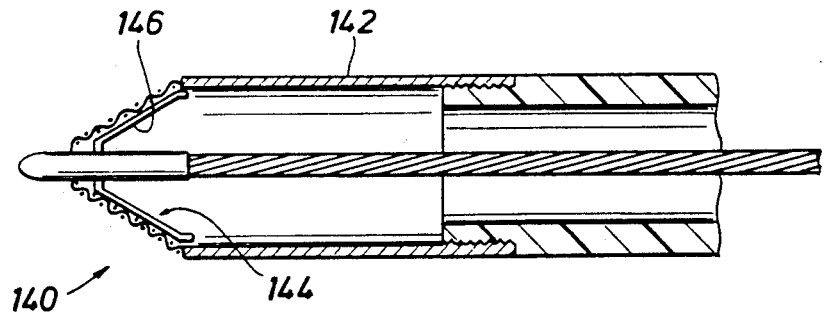
FIG. 8 is a partial side view of yet another alternate embodiment of the cutting head of the invention.

FIG. 8 is a similar embodiment 140 except that the housing 142 and cutter head 144 are generally hollow and it may have a passage for a guide wire. The surface of the conical cutter element may be provided with diamond or tungsten carbide burrs or may be a V-shaped knife having two cutting edges 146 located diametrically opposite one another for cutting any material entering through the conic screen. The screen defines openings of specified size to enable material entry and subsequent cutting. This furnishes holes of the appropriate size to enable occlusive material cutting. As before, cuttings are flushed to the rear of the tool and vacuum removed.

Figure 9:
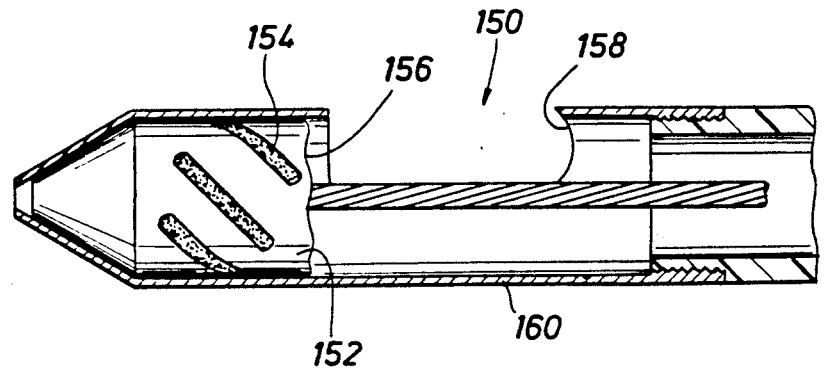
FIG. 9 is a partial side view of another embodiment of the cutting head of the invention.

FIG. 9 is another variation on essentially the same theme, except in this embodiment 150, the substantially cylindrical shape of the cutter element 152 is constructed with either diagonal or horizontal cutting members 154 about the body of the cutting element. The diagonal or horizontal cutters 154 may be sharply honed to allow the cutter to be rotated or oscillated against a particularly hard material such as calcific or boney material while in contact. In this version a grinding, grating or sanding action is achieved instead of cutting. Cutter reciprocation to and fro will cut or abrade the occlusive material. The back edge 156 is again serrated to cut material extending through the window 158 of the housing 160.

While the foregoing is directed to the preferred and illustrated embodiments, the scope is determined by the claims which follow.

What is claimed is:

1. An atherectomy catheter for removal of occlusive material in a blood vessel, tract, or cavity, comprising:
   (a) a catheter tube;
   (b) a cutter head assembly mounted on the distal end of said catheter tube for excising occlusive material blocking the blood vessel, tract or cavity;
   (c) flexible drive means extending through said catheter tube;
   (d) a rotary cutter housed within said cutter head assembly and connected to said flexible drive means;
   (e) power means connected to the proximal end of said catheter tube for rotating and reciprocating said rotary cutter;
   (f) a pair of bendable wires extending externally along said cutter head assembly, wherein upon actuation said wires bow outwardly against the interior wall of the blood vessel, tract or cavity for urging said cutter head assembly laterally against the occlusive material; and
   (g) means connected to said catheter tube for evacuating the excised occlusive material from the blood vessel, tract or cavity.

2. The catheter of claim 1 wherein said cutter head assembly comprises an elongate, generally cylindrical housing having an opening extending longitudinally along one side of said housing for admitting occlusive material to the interior of said housing, and wherein said rotary cutter cuts occlusive materials into particles sufficiently small for evacuating through said catheter tube.

3. The apparatus of claim 2 including a control line extending along said catheter tube to control extension of said pair of wires.

4. The apparatus of claim 3 wherein said pair of wires extend on one side of said housing diametrically opposite said opening for admitting occlusive material into the interior of said housing.

5. The apparatus of claim 4 wherein said rotary cutter has a rearwardly facing cutting means for cutting material protruding through said opening into the interior of said housing.

6. The apparatus of claim 1 wherein said cutter head assembly includes a side loaded laterally opening port thereinto for receiving occlusive material thereinto for cutting and removal.

7. The apparatus of claim 1 wherein said cutter head assembly has a selected set of openings formed in the outer surface thereof wherein the outer surface is otherwise a solid member to enable occlusive material to extend thereinto for subsequent removal.

8. The apparatus of claim 1 wherein said rotary cutter connects with and is rotated by said flexible drive means and said cutter includes at least one sharp edge moving in near proximity of said cutter head assembly to serve as a cutter for occlusive material.

9. The apparatus of claim 1 including a motorized means for forming rotary motion imparted to a coupling means wherein said coupling means connects with said elongate flexible drive means and said drive means extends along and within said outer catheter tube to thereby impart rotative cutting action to said cutter head assembly, and said cutter head assembly is affixed to the end of said outer catheter tube with said flexible drive means extending therealong for rotative motion therein.

10. Apparatus for removal of occlusive material located in a vessel, cavity or other region of the body wherein entry is via an elongate catheter, comprising:
    (a) an elongate hollow catheter tube;
    (b) a cutting head assembly attached to an end of said catheter tube and comprising:
    (1) an elongate housing defining said assembly;
    (2) window means formed in said housing, said window means being positioned to admit occlusive material into said housing, wherein said window means comprises a plurality of openings permitting occlusive material to pass therethrough into the path of said cutting means;
    (c) rotatable cutting means mounted in said housing and having a cutting edge for cutting occlusive material;
    (d) power means connected to an end of said catheter tube;
    (e) an elongate power drive means in said tube connected from said power means to said cutting means to rotate said cutting means;
    (f) means positioning said cutting means in said housing for reciprocating movement to thereby enable cutting of the occlusive material;
    (g) means urging said cutting head assembly toward the occlusive material causing the occlusive material to align adjacent said window for cutting by said cutting means; and
    (h) means connected to said catheter tube for evacuating occlusive material cut by said cutting head.

11. The apparatus of claim 10 wherein said rotatable cutting means includes a forwardly located cutting edge, and a rearwardly located cutting edge wherein said rearwardly located cutting edge engages the occlusive material on retraction of said cutting means.

12. The apparatus of claim 10 wherein said cutting head assembly includes a side opening window formed in said elongate cylindrical housing.

13. The apparatus of claim 10 wherein said housing has a conic leading end portion with said window means at least partially deployed over said conic portion.

14. The apparatus of claim 11 wherein said elongate housing is an elongate cylindrical hollow body, and said side opening window encircles approximately one half the circumference thereof, and wherein said housing includes a forwardly located full circle portion of said housing and said side opening window is to the rear thereof.

15. An atherectomy catheter for removal of occlusive material in a blood vessel, tract, or cavity comprising:
    (a) a catheter tube;
    (b) a cutter head housing attached to the distal end of said catheter tube;
    (c) flexible drive means extending through said catheter tube;
    (d) a rotary cutter housed within said cutter head housing and connected to said flexible drive means;
    (e) power means connected to the proximal end of said catheter tube for rotating and reciprocating said rotary cutter within said cutter head housing for excising occlusive material blocking the blood vessel, tract or cavity;

(f) externally mounted resilient means for urging said cutter head housing laterally, wherein said resilient means comprises a pair of bendable wires extending externally along said housing, wherein upon actuation said wires bow outwardly against the interior wall of the blood vessel, tract or cavity for urging said cutter head housing laterally against the occlusive material; and (g) means connected to said catheter tube for evacuating the excised occlusive material from the blood vessel, tract or cavity.

* * * * *